(12) United States Patent
Satya (10) Patent No.: US 10,160,998 B2
(45) Date of Patent: Dec. 25, 2018

(54) PCR PRIMERS CONTAINING CLEAVABLE NUCLEOTIDES

(71) Applicant: QIAGEN SCIENCES LLC, Germantown, MD (US)

(72) Inventor: Ravi Vijaya Satya, Montgomery Village, MD (US)

(73) Assignee: QIAGEN Sciences, LLC, Germantown, MD (US)

( * ) Notice: Subject to any disclaimer, the term of this patent is extended or adjusted under 35 U.S.C. 154(b) by 669 days.

(21) Appl. No.: 14/614,680

(22) Filed: Feb. 5, 2015

(65) Prior Publication Data

US 2015/0225775 A1    Aug. 13, 2015

Related U.S. Application Data

(60) Provisional application No. 61/936,973, filed on Feb. 7, 2014.

(51) Int. Cl.
*C12P 19/34*    (2006.01)
*C12Q 1/686*    (2018.01)

(52) U.S. Cl.
CPC .................................... *C12Q 1/686* (2013.01)

(58) Field of Classification Search
USPC ............................................. 435/6.12, 91.2
See application file for complete search history.

(56) References Cited

U.S. PATENT DOCUMENTS

| | | | |
|---|---|---|---|
| 2003/0219770 A1* | 11/2003 | Eshleman | C12Q 1/6869 435/6.14 |
| 2008/0311628 A1 | 12/2008 | Shoemaker | |
| 2010/0129874 A1 | 5/2010 | Mitra et al. | |
| 2012/0053064 A1 | 3/2012 | Highsmith, Jr. et al. | |
| 2012/0295819 A1* | 11/2012 | Leamon | C12Q 1/6806 506/26 |
| 2013/0005613 A1 | 1/2013 | Leamon et al. | |

FOREIGN PATENT DOCUMENTS

| | | |
|---|---|---|
| WO | 92/18521 A1 | 10/1992 |
| WO | 03/056030 A2 | 7/2003 |
| WO | 2005/076925 A1 | 8/2005 |
| WO | 2012/078312 A2 | 6/2012 |
| WO | 2013/081755 A1 | 6/2013 |
| WO | 2013/081864 A1 | 6/2013 |
| WO | 2014/012107 A2 | 1/2014 |

OTHER PUBLICATIONS

Booth et al., "Assembly and cloning of coding sequences for neurotrophic factors directly from genomic DNA using polymerase chain reaction and uracil DNA glycosylase," *Gene* 146(2):303-308, Sep. 2, 1994, 1 page. (Abstract Only).
Buchman et al., "Selective RNA Amplification: A Novel Method Using dUMP-containing Primers and Uracil DNA Glycosylase," *PCR Methods and Applications* 3:28-31, 1993.
Longo et al., "Use of uracil DNA glycosylase to control carry-over contamination in polymerase chain reactions," *Gene* 93:125-128, 1990.
Owen et al., "A Highly Efficient Method of Site-Directed Mutagenesis Using PCR and UDG Cloning," *Focus* 16(2):39-44, 1994.
Rashtchian et al., "Uracil DNA Glycosylase-Mediated Cloning of Polymerase Chain Reaction-Amplified DNA: Application to Genomic and cDNA Cloning," *Analytical Biochemistry* 206(1):91-97, 1992.
Smith et al., "Generation of Cohesive Ends on PCR Products by UDG-mediated Excision of dU, and Application for Cloning into Restriction Digest-linearized Vectors," *Genome Research* 2:328-332, 1993.
Varley et al, "Nested Patch PCR enables highly multiplexed mutation discovery in candidate genes," *Genome Research* 18:1844-1850, 2008.

* cited by examiner

*Primary Examiner* — Kenneth R Horlick
(74) *Attorney, Agent, or Firm* — Seed IP Law Group LLP (57) ABSTRACT

The present disclosure provides methods, compositions, and kits for performing PCR (including multiplex PCR). The methods, compositions and kits provided herein use one or more primer pairs that contain one or more cleavable bases located at a minimal distance away from the 3' termini of the primers, and increase the accuracy of downstream analysis of sequence data.

9 Claims, 8 Drawing Sheets

Specification includes a Sequence Listing.

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Primer sequence

<400> SEQUENCE: 1
tgcagataac ttgactttcc ttc     23

```
<210> SEQ ID NO 2
<211> LENGTH: 55
<212> TYPE: DNA
<213> ORGANISM: Artificial Sequence
<220> FEATURE:
<223> OTHER INFORMATION: Synthetized sequence

<400> SEQUENCE: 2
catgcagata acttgacttt ccttctcttc tcctcctttc tgtcctcagg tgacg          55
```

PCR PRIMERS CONTAINING CLEAVABLE NUCLEOTIDES

STATEMENT REGARDING SEQUENCE LISTING

The Sequence Listing associated with this application is provided in text format in lieu of a paper copy, and is hereby incorporated by reference into the specification. The name of the text file containing the Sequence Listing 830109_406_SEQUENCE_LISTINGa.txt. The text file is 4 KB, was created on Apr. 10, 2015, and is being submitted electronically via EFS-Web.

BACKGROUND

Technical Field

The present disclosure relates to methods, compositions, and kits for performing PCR, including multiplex PCR.

Description of the Related Art

PCR, especially multiplex PCR, is one of the technologies used for target enrichment to selectively sequence specific regions of interest in genome. The primer sequences used in PCR are considered to be of no use for downstream analysis, and are often removed through enzymatic digestion before the sequencing step so that sequencing capacity is not wasted in sequencing the primer bases.

The primer removal step is accomplished by substituting one or two Thymine (T) bases in the primer with Uracil (U) bases. The PCR reaction proceeds as usual, incorporating Adenine (A) bases into the PCR product at positions complementary to the U bases in the primer. After the PCR step, the double stranded DNA product is treated with uracil-N-glycosylase (UNG, also known as uracil-DNA glycosylase (UDG)), which causes degradation of the primer strand until the furthest 3' U base, resulting in single-stranded overhangs at both ends of the double-stranded DNA molecule. These single-stranded overhangs are then removed using exonuclease. To minimize the waste of sequencing capacity in sequencing the primer bases, a U base is typically placed as close to the 3' terminus of the primer as possible.

BRIEF SUMMARY

The present disclosure provides methods, sets of primer pairs, reaction mixtures, and kits for performing PCR, including singleplex and multiplex PCR. All or substantially all of the primers contain one or more cleavable nucleotides that are located at a minimal distance (e.g., 4 nucleotides) away from the 3' termini of the primers. PCR using such primer pairs improves the accuracy of downstream analysis of sequence data.

In one aspect, the present disclosure provides a method for performing polymerase chain reaction (PCR), comprising:

a) amplifying one or more different target nucleic acids in the presence of one or more different primer pairs specific to the one or more different target nucleic acids in a single reaction mixture via PCR, wherein each primer of the one or more different primer pairs contains one or more cleavable bases, and wherein in substantially all of the primers of the one or more different primer pairs, each of the one or more cleavable bases is at least 4 nucleotides away from the 3' terminus of the primer that comprises the one or more cleavable bases.

In certain embodiments, in substantially all of the primers of the one or more different primer pairs, each of the one or more cleavable bases is at least 5 nucleotides away from the 3' terminus of the primer that comprises the one or more cleavable bases. In certain other embodiments, in substantially all of the primers of the one or more different primer pairs, each of the one or more cleavable bases is at least 6 nucleotides away from the 3' terminus of the primer that comprises the one or more cleavable bases. In certain other embodiments, in substantially all of the primers of the one or more different primer pairs, each of the one or more cleavable bases is at least 7 nucleotides away from the 3' terminus of the primer that comprises the one or more cleavable bases. In certain other embodiments, in substantially all of the primers of the one or more different primer pairs, each of the one or more cleavable bases is at least 8 nucleotides away from the 3' terminus of the primer that comprises the one or more cleavable bases.

Step a) may comprise amplifying a single target nucleic acid in the presence of a primer pair specific to the single target nucleic acid in the single reaction mixture. Alternatively, step a) may comprise amplifying a plurality of different primer pairs specific to the plurality of different target nucleic acids in the single reaction mixture.

In certain embodiments, in all of the primers of the one or more different primer pairs, each of one or more cleavable bases is at least 4 nucleotides away from the 3' terminus of the primer that comprises the one or more cleavable bases. In certain other embodiments, in all of the primers of the one or more different primer pairs, each of one or more cleavable bases is at least 5 nucleotides away from the 3' terminus of the primer that comprises the one or more cleavable bases. In certain other embodiments, in all of the primers of the one or more different primer pairs, each of one or more cleavable bases is at least 6 nucleotides away from the 3' terminus of the primer that comprises the one or more cleavable bases. In certain other embodiments, in all of the primers of the one or more different primer pairs, each of one or more cleavable bases is at least 7 nucleotides away from the 3' terminus of the primer that comprises the one or more cleavable bases. In certain other embodiments, in all of the primers of the one or more different primer pairs, each of one or more cleavable bases is at least 8 nucleotides away from the 3' terminus of the primer that comprises the one or more cleavable bases.

Preferably, the cleavable base is uracil. Alternatively, the cleavable base is inosine, an oxidized pyrimidine, an oxidized purine, 5-hydroxyuracil, 5-hydroxylmethyluracil, or 5-formyluracil.

The one or more different primer pairs may comprise at least 100 different primer pairs.

The method disclosed herein may further comprise one or more:

b) cleaving the one or more cleavable bases in the amplification product(s) of step a) to produce single-stranded DNA overhangs in the amplification product(s), c) digesting the single stranded DNA overhangs obtained in step b) to generate trimmed amplification product(s), d) ligating adapters to the trimmed amplification product(s) to produce adapter-linked trimmed amplification product(s), and e) sequencing the adapter-linked trimmed amplification product(s) of step d).

In another aspect, the present disclosure provides a primer pair set, comprising:

one or more of different primer pairs specific for one or more different target nucleic acids, wherein each primer of the one or more different primer pairs contains one or more cleavable bases, and wherein in substantially all of the primers of the one or more different primer pairs, each of the one or more cleavable bases is at least 4 nucleotides away from the 3' terminus of the primer that comprises the one or more cleavable bases.

In certain embodiments, in substantially all of the primers of the one or more different primer pairs, each of the one or more cleavable bases is at least 5 nucleotides away from the 3' terminus of the primer that comprises the one or more cleavable bases. In certain other embodiments, in substantially all of the primers of the one or more different primer pairs, each of the one or more cleavable bases is at least 6 nucleotides away from the 3' terminus of the primer that comprises the one or more cleavable bases. In certain other embodiments, in substantially all of the primers of the one or more different primer pairs, each of the one or more cleavable bases is at least 7 nucleotides away from the 3' terminus of the primer that comprises the one or more cleavable bases. In certain other embodiments, in substantially all of the primers of the one or more different primer pairs, each of the one or more cleavable bases is at least 8 nucleotides away from the 3' terminus of the primer that comprises the one or more cleavable bases.

In certain embodiments, in all of the primers of the one or more different primer pairs, each of the one or more cleavable bases is at least 4 nucleotides away from the 3' terminus of the primer that comprises the one or more cleavable bases. In certain other embodiments, in substantially all of the primers of the one or more different primer pairs, each of the one or more cleavable bases is at least 6 nucleotides away from the 3' terminus of the primer that comprises the one or more cleavable bases. In certain other embodiments, in substantially all of the primers of the one or more different primer pairs, each of the one or more cleavable bases is at least 7 nucleotides away from the 3' terminus of the primer that comprises the one or more cleavable bases. In certain other embodiments, in substantially all of the primers of the one or more different primer pairs, each of the one or more cleavable bases is at least 8 nucleotides away from the 3' terminus of the primer that comprises the one or more cleavable bases.

Preferably, the cleavable nucleotide is uracil.

The primer pair set may comprise at least 100 different primer pairs.

In another aspect, the present disclosure provides a PCR reaction mixture, comprising: the primer pair set provided herein, a DNA polymerase, dNTPs, and a PCR reaction buffer.

In another aspect, the present disclosure provides a kit for performing PCR comprising the primer pair set provided herein.

The kit may further comprise one or more of the following:

a mixture that comprises dNTPs and a PCR reaction buffer, a DNA polymerase, a cleaving reagent capable of cleaving the cleavable bases in the primers, and one or more of enzymes capable of fragmenting abasic site-containing nucleic acids at the abasic sites, endonucleases capable of degrading single-stranded overhangs, and ligases.

DETAILED DESCRIPTION

PCR, especially multiplex PCR, is often used for target enrichment to selectively amplify specific regions of interest for downstream sequencing analysis. To minimize waste of sequence capacity in sequencing the primer bases, primers having one or more of the U bases at or close to their 3' termini are used to facilitate their subsequent removal.

Figure 1:
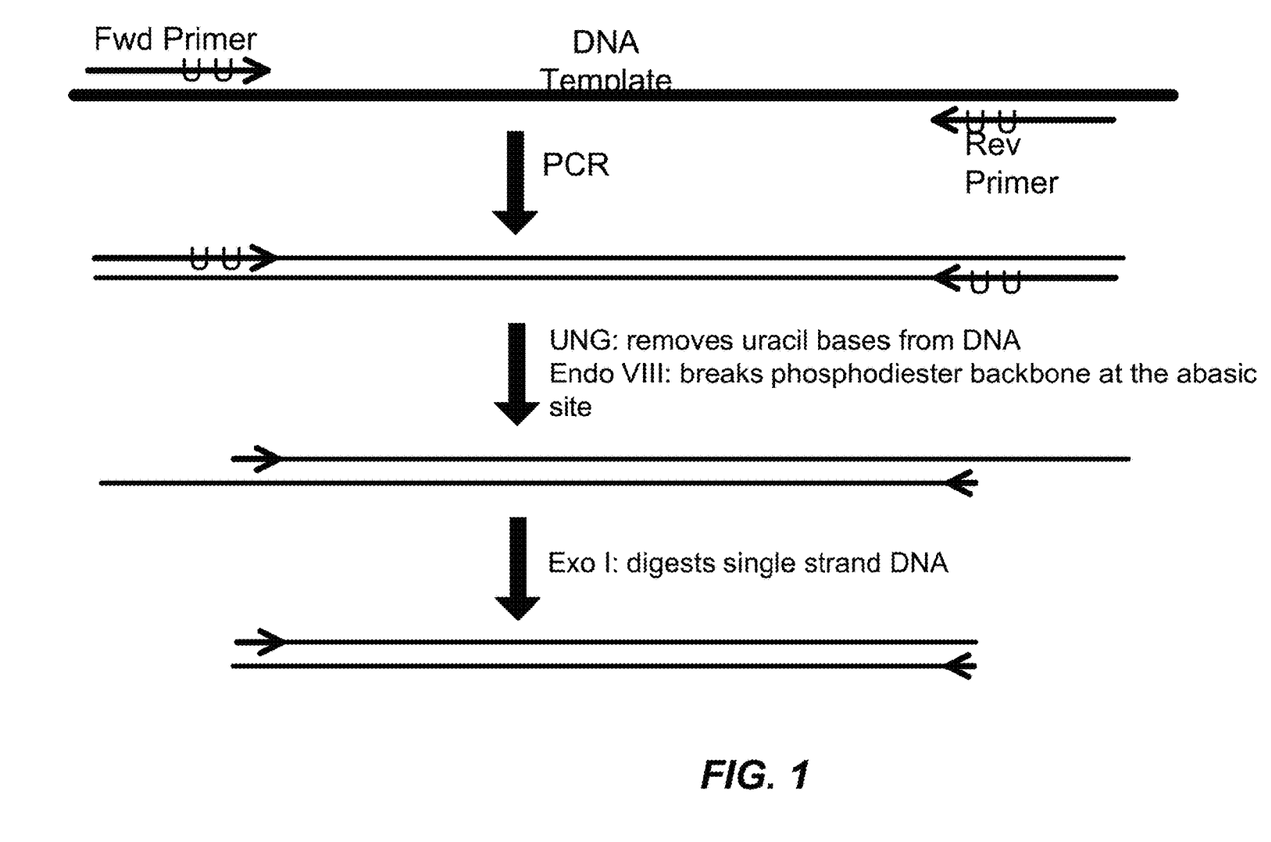
FIG. 1 is a schematic presentation of a method for performing a PCR reaction using two primers each having a U base at or close to their 3' termini.

For example, FIG. 1 is a representative method of performing PCR using a forward primer ("Fwd Primer") and a reverse primer ("Rev Primer") each having two U bases, one of which is very close to the 3' terminus of the primer (e.g., only 1 nucleotide away from the 3' terminus). The PCR reaction results in PCR products that contain the two primers at their 5' ends of each strand. Such PCR products may be treated with UNG to remove the U bases in the primer strand followed by the treatment of Endonuclease VIII to break phosphodiester backbone at the abasic sites. The resulting single-stranded overhangs at each end of the PCR products may be removed using an exonuclease (e.g., Exo I). The blunt-ended PCR products may then be linked to adaptors, optionally amplified, and subsequently sequenced.

Figure 2:
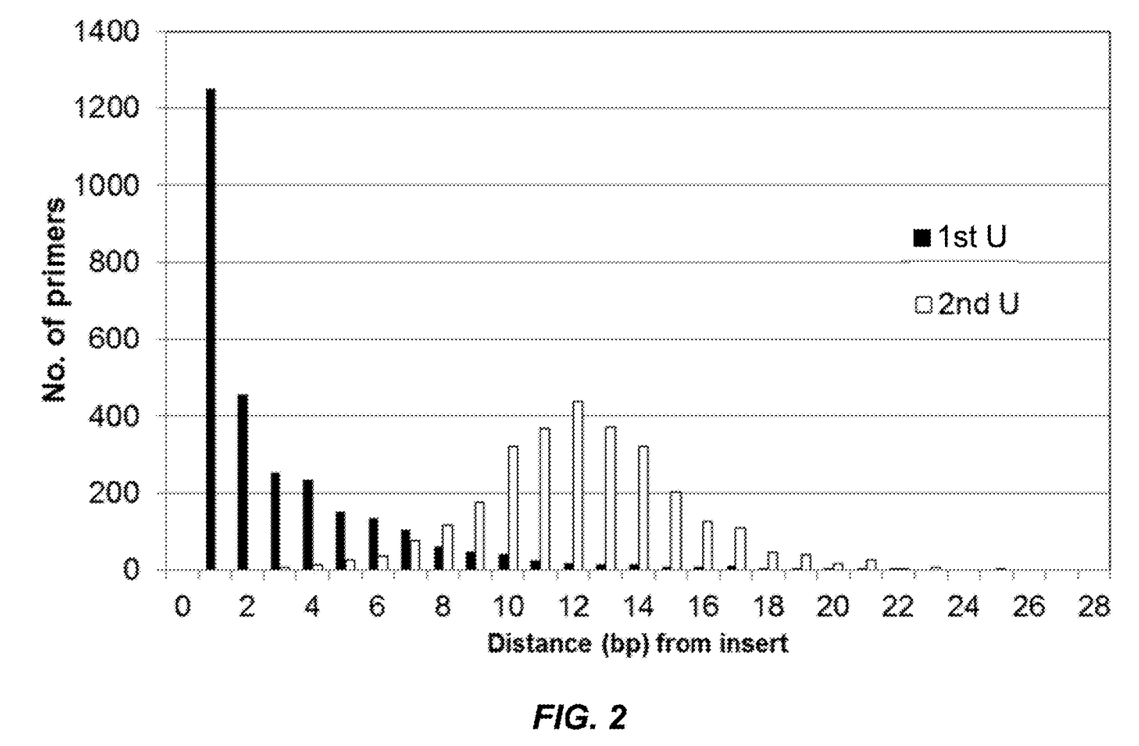
FIG. 2 is a graph showing the distribution of the U bases in a lung cancer panel. The panel has a total of 1419 primers in four pools.
Figure 3:
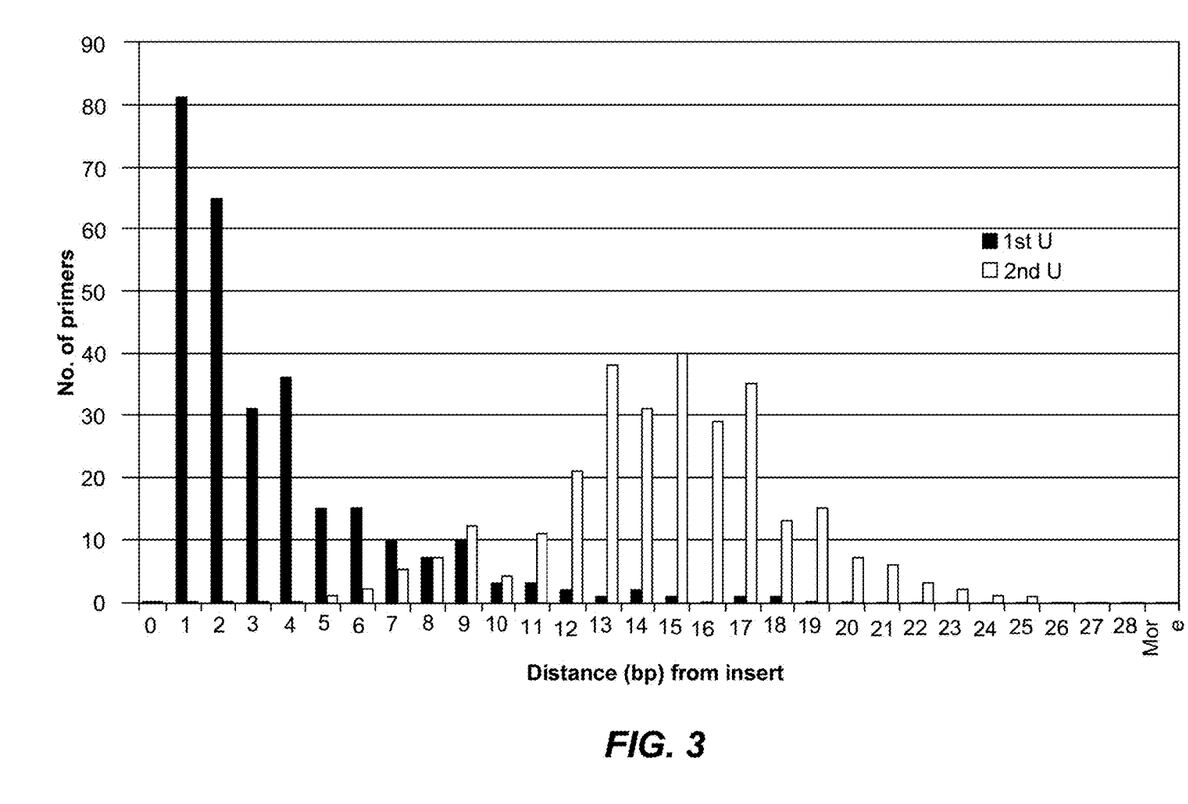
FIG. 3 is a graph showing the distribution of the U bases in the AmpliSeq panel IAD28828 (Life Technologies Corporation). The panel has a total of 142 primer pairs in two pools.

It is general practice to place the U bases as close to the 3' terminus as possible to minimize the number of read bases that are wasted in sequencing the primer. FIG. 2 shows the distribution of the two U bases in a lung cancer panel, when the first base is placed as close to the 3' terminus of the primer as possible. FIG. 3 shows the distribution of U bases in a panel designed by Life Technologies Corporation. It can be seen from FIG. 3 that the most common scenario is to place the U base just one nucleotide away from the 3' terminus, thus showing the lack of attempt to enforce a minimum distance between the U base and the 3' terminus in the design. The distance between the first U base and the 3' terminus is at most 3 nucleotides for more than 60% of the primers.

Although removing primers as much as possible after PCR amplification and prior to sequencing reactions makes optimal use of sequencing capacity by minimizing the read bases used for sequencing the primer and maximizing the read bases used for sequencing the template, the present inventor found that digesting the primers in their entirety leads to multiple problems in downstream analysis of sequence data. These problems include: 1) inaccurate alignments towards the ends of amplified target nucleic acids, which result in both false-positives and false-negatives in variant calls; and 2) low base alignment quality scores near the ends of the read, which result in false-negatives in variant calls.

Figure 4:
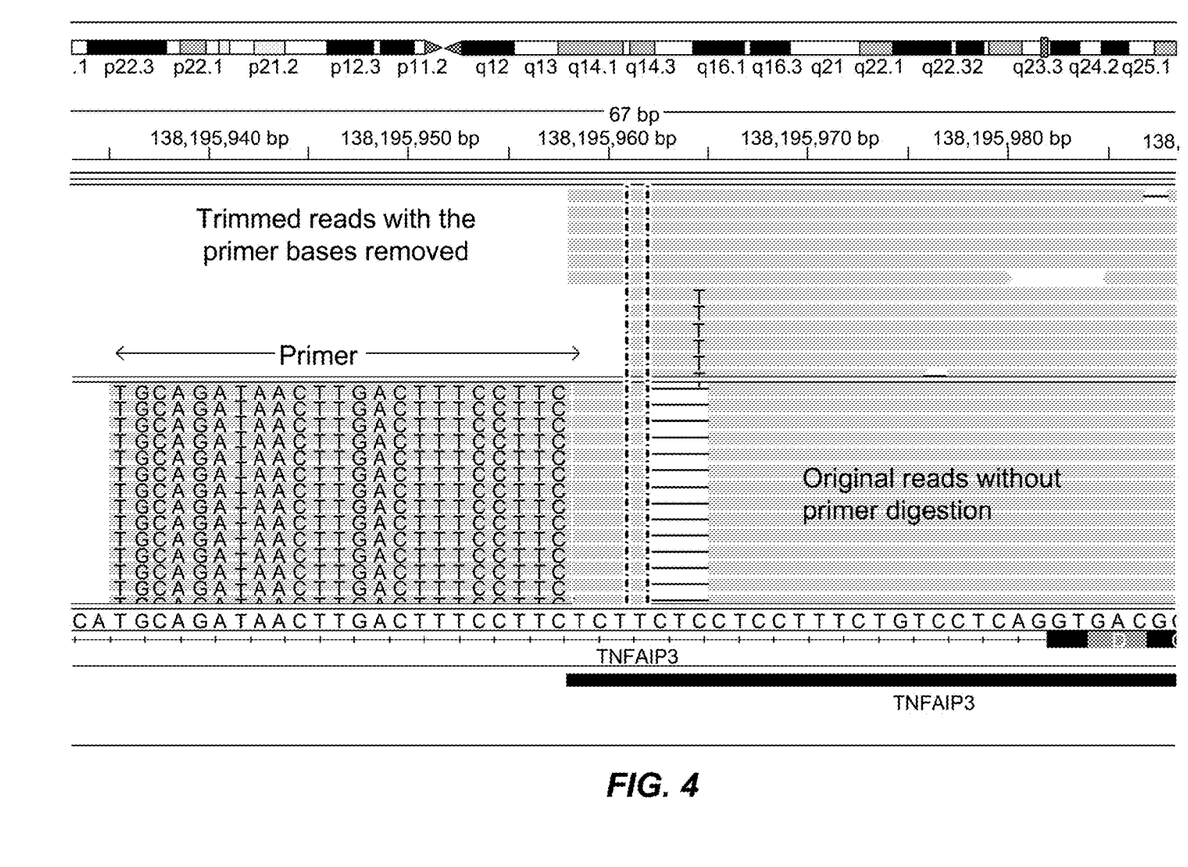
FIG. 4 shows an exemplary scenario where removal of primer bases results in a false-negative deletion and a false-positive single nucleotide polymorphism (SNP). The primer sequence (5'-TGCAGATAACTTGACTTTCCTTC-3') is set forth in SEQ ID NO:1, while the nucleic acid sequence (5'-CATGCAGATAACTTGACTTTCCTTCTCT-TCTCCTCCTTTCTGTCCTCAGGTGAC G-3') is set forth in SEQ ID NO:2.

For example, as described in more detail in the Examples, the comparison between reads generated without primer removal and containing the complete primer sequences (referred to as "untrimmed reads") and those without the primer sequences (referred to as "trimmed reads") shows that the removal of the primer bases resulted in a false-negative deletion (i.e., a deletion of "CTC") and a false-positive SNP (i.e., a CT substitution) (see, FIG. 4). Thus, the lack of primer bases causes misalignments towards the ends of the trimmed reads, resulting in missing the deletion altogether but calling a SNP instead.

Figure 5A:
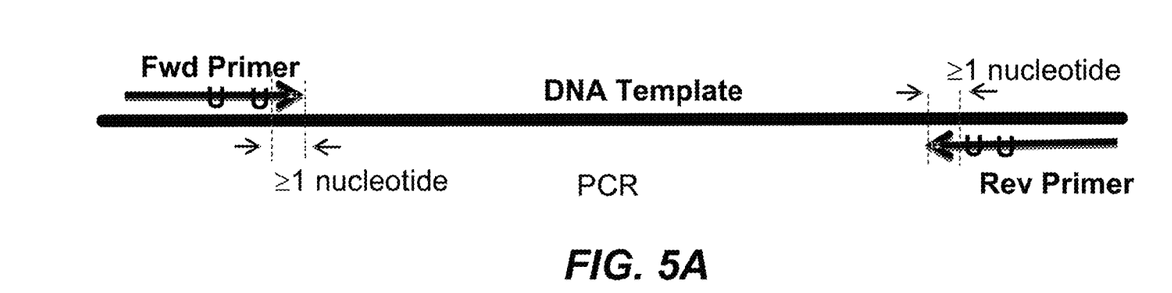
FIG. 5A is a schematic presentation of a prior art primer pair where in each primer, the first U base is placed as close to the 3' terminus of the primer as possible, and can be as close as just 1 nucleotide away from the 3' terminus depending on the primer sequence.
Figure 5B:
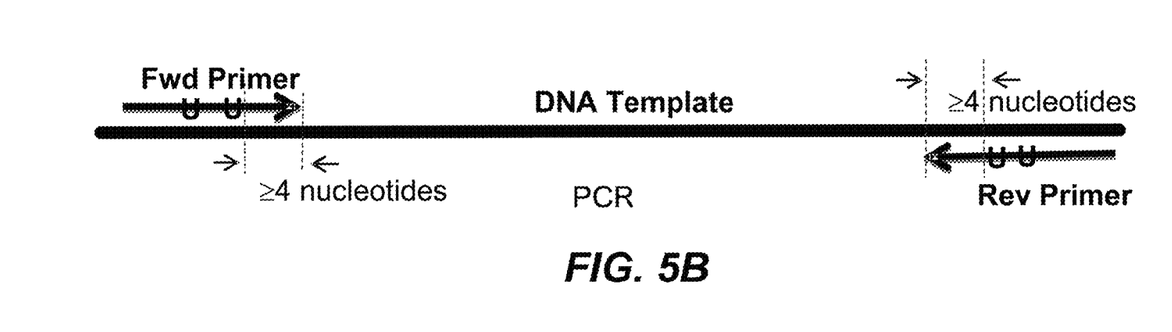
FIG. 5B is a schematic presentation of an exemplary primer pair disclosed herein where a minimum distance of 4 nucleotides is maintained between the 3' terminus of the primer and the first U base to avoid most sequence alignment problems.

To ensure that a minimum number of primer bases are left undigested in the enzymatic digestion step and thus prevent inaccurate variant calls resulting from misalignments towards the ends of trimmed reads, the present disclosure provides primers designed so that the U base (or another cleavable base) for enzymatic digestion is at least 4 bases away from the 3' termini of the primers (see FIG. 5B). Compared with prior art primers (see FIG. 5A), such primers help in obtaining accurate alignments near the ends of a target nucleic acid, thereby avoiding the false-positives and false-negatives in variant calls. The primer bases also help in avoiding low base alignment quality scores near the ends of the target nucleic acid.

In one aspect, the present disclosure provides a method for performing polymerase chain reaction (PCR) that comprises amplifying one or more different target nucleic acids in the presence of one or more different primer pairs that are specific to the one or more of different target nucleic acids via PCR, wherein each primer of the one or more different primer pairs contains one or more cleavable bases, and wherein in substantially all of the primers of the one or more different primer pairs, each of the one or more cleavable bases is at least 4 nucleotides (e.g., at least 5, 6, 7, 8, or more nucleotides) away from the 3' terminus of the primer that comprises the one or more cleavable bases.

Polymerase chain reaction (PCR) is a well-known technique for amplifying a DNA molecule to generate multiple copies of the DNA molecule (see, U.S. Pat. Nos. 4,683,195 and 4,683,202). It relies on thermal cycling consisting of cycles of repeated heating and cooling of the reaction for DNA melting and enzymatic replication of the DNA. PCR uses primers containing sequences complementary to a target region along with a DNA polymerase. As PCR progresses, the DNA generated is itself used as a template for replication, setting in motion a chain reaction in which the DNA template is exponentially amplified.

In certain embodiments, the method provided herein is for performing a singleplex PCR. A "singleplex PCR" refers to a PCR reaction that amplifies a single target nucleic acid in the presence of a primer pair specific to the target nucleic acid.

In certain other embodiments, the method provided herein is for performing a multiplex PCR. Multiplex PCR is a type of PCR that uses multiple primers within a single PCR mixture and a temperature-mediated DNA polymerase in a thermal cycler to amplify multiple target DNA molecules.

Target nucleic acids to be amplified in PCR may be prepared from any samples. Exemplary samples from which target nucleic acids may be prepared include, but are not limited to, blood, swabs, body fluid, tissues including but not limited to, liver, spleen, kidney, lung, intestine, brain, heart, muscle, and pancreas, cell cultures, plant tissues or samples, as well as lysates, extracts, or materials and fractions obtained from the samples described above, or any cells, microorganisms and viruses that may be present on or in a sample, and the like.

Materials obtained from clinical or forensic settings that contain nucleic acids are also within the intended meaning of the term "sample" from which a genomic DNA sample may be prepared. Preferably, the sample is a biological sample derived from a human, animal, plant, bacteria or fungi. The term "sample" also includes processed samples including preserved, fixed and/or stabilized samples, such as formalin fixed and paraffin-embedded (FFPE samples) and other samples that were treated with cross-linking fixatives such as glutaraldehyde.

Isolating target nucleic acids from a sample of interest may be performed by any method known in the art useful for nucleic acid isolation or purification. In addition, many kits for nucleic acid preparation are commercially available and may be used, including QIAamp DNA mini kit, QIAamp FFPE Tissue kit, and PAXgene DNA kit.

Target nucleic acids may include one or more genes of interest or regions or fragments thereof. For multiplex PCR, the number of genes in the target nucleic acid to be amplified in a single reaction may vary. For example, the minimum number of different genes in the target nucleic acids to be amplified in a single multiplex PCR reaction may be 2, 3, 4, 5, 6, 7, 8, 9, 10, 15, 20, 25, 30, 35, 40, 45, or 50. The maximum number of different genes in the target nucleic acids to be amplified in a single multiplex PCR reaction may be 75, 100, 150, 200, 300, 400, 500, 600, 700, 800, 900, 1000, 1500, or more. In certain embodiments, the number of genes in the target nucleic acid to be amplified in a single multiplex PCR reaction is between 10 and 50, between 50 and 100, between 100 and 200, between 200 and 500, or between 500 and 1000. In a preferred embodiment, the number of genes in the target nucleic acid to be amplified in a single multiplex PCR reaction is between 10 and 200, more preferably between 25 and 100.

In certain embodiments, more than one region in a gene of interest is amplified in a single multiplex PCR reaction. For example, a single multiplex PCR may be used to amplify one or more genes each having multiple mutations of interest, including those involved in predicting disease risks or responsiveness to certain treatments. Thus, the present disclosure also includes performing multiple PCR wherein multiple regions (e.g., at least 5, 10, 15, 20, 25, 30, 35, 40, 45, or 50) of a single gene are amplified. Preferably, a single multiplex PCR reaction amplifies overlapping exonic portions of a gene or genes that cover the complete or substantially complete (e.g., at least 85%, at least 90%, or at least 95% of) exonic regions of the gene or genes. Such a design maximizes target coverage and minimizes nonspecific amplification.

The multiplex PCR reaction according to the present disclosure may also amplify multiple genes of interest, some but not all of which have multiple regions to be amplified. In certain other embodiments, the multiplex PCR reaction according to the present disclosure may amplify multiple genes of interest, all of which have multiple regions to be amplified.

Any genes of interest may be amplified according to the method provided herein. Genes particularly of interest are those known to be involved in diseases or disorders, including those mutations of which are associated with diseases or disorders or sensitivity or resistance to certain treatments. The diseases or disorders may be any diseases or disorders of interest, including but not limited to various types of cancers (e.g., human breast cancer, colon cancer, leukemia, liver cancer, lung cancer, ovarian cancer, prostate cancer, and gastric cancer), inherited disorders, neurological, metabolic, neuromuscular, developmental, cardiovascular, and autoimmune disorders.

Exemplary genes of interest include but are not limited to EGFR, BRAF, KRAS, ERBB2, PDGFRA, TP53, BRAC1, and BRAC2. Additional genes of interest include those disclosed in U.S. Patent Publication No. US 2013/0005613, which is incorporated by reference.

PCR reactions as provided herein use one or more primer pairs that are specific for one or more target nucleic acids. A "primer" is an oligonucleotide that is complementary to a target nucleic acid and leads to addition of nucleotides to the 3' end of the primer in the presence of a DNA polymerase using the target nucleic acid as a template.

An "oligonucleotide" refers to a short polymer composed of deoxyribonucleotides, ribonucleotides or combinations thereof. Oligonucleotides are generally between about 10 to about 100 nucleotides, preferably about 12 to about 50 nucleotides, more preferably about 15 to about 30 nucleotides, in length.

A "primer pair" is a pair of primers, one of which is complementary to one strand of a target nucleic acid, and the other is complementary to the other strand of the target nucleic acid if the target nucleic acid is double-stranded or to a strand that is complementary to the target nucleic acid if the target nucleic acid is single-stranded. The extension of both primers amplifies the target nucleic acid or a portion thereof in a PCR reaction.

A primer pair "specific for amplifying" a target nucleic acid or a primer pair "specific to" a target nucleic acid refers to a primer pair capable of specifically amplifying the target nucleic acid or a fragment thereof.

"Specifically amplifying" a target nucleic acid means amplifying the target nucleic acid or a nucleic acid that is nearly identical to (i.e., at least 95% identical to) the target nucleic acid without amplifying other nucleic acids in a reaction mixture.

For determining sequence identity, the WU-BLAST-2 program (Altschul et al., Methods in Enzymology 266:460-480, 1996) is used. This program uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. A percent nucleic acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The terms "complementary" and "complement" and their variants, as used herein, refer to any two nucleic acid sequences or portions thereof that form a hybridized duplex by base pairing. One nucleic acid fragment may be completely complimentary to another nucleic acid fragment if all of the nucleotides in the fragment form base pairing with nucleotides in the corresponding antiparallel positions on the other nucleic acid fragment. "Partial" complementarity describes nucleic acid sequences in which at least 50%, but less than 100%, of the residues of one nucleic acid fragment are complementary to residues in the other nucleic acid fragment. A primer is "substantially complementary" to a target nucleic acid if at least 85% of the residues of the primer are complementary to residues in the target nucleic acid.

In some embodiments, at least 50%, but less than 100%, of the residues of a primer are complementary to residues in a target nucleic acid. In some embodiments, at least 70%, 75%, 80%, 85%, 90%, 95% or 98%, but less than 100%, of the residues of a primer are complementary to residues in a target nucleic acid. In preferred embodiments, a primer is completely complementary to a target nucleic acid.

For multiplex PCR, the number of primer pairs in a single multiplex PCR reaction may vary depending on the number of target nucleic acids to be amplified. For example, the minimum number of different primer pairs in a single multiplex PCR reaction may be 10, 20, 30, 40, 50, 100, 200, 300, 400, 500, 600, 700, 800, 900, 1000, 1500, 2000, 2500, or 3000. The maximum number of different primers in a single multiplex PCR reaction may be 4000, 5000, 6000, 7000, 8000, 9000, 10000 or more. In certain embodiments, the number of primer pair in a single multiplex PCR reaction is between 50 and 500, between 500 and 1000, between 1000 and 2000, between 2000 and 3000, between 3000 and 4000, between 4000 and 5000, between 5000 and 6000, between 6000 and 7000, between 7000 and 8000, between 8000 and 9000, and between 9000 and 10000. In a preferred embodiment, the number of different target nucleic acids to be amplified in a single multiplex PCR reaction is between 100 and 10000, such as between 100 and 9000, between 200 and 8000, between 1000 and 7000, and between 2000 and 6000.

The number of different genes in target nucleic acids to be amplified in a single multiplex PCR reaction may also vary. Such a number may be between 5 and 1000, such as between 5 and 10, between 10 and 50, between 50 and 100, between 100 and 200, between 200 and 400, between 400 and 600, between 600 and 800, and between 800 and 1000. Preferably, the number of different genes to be amplified in a single multiplex PCR reaction is between 10 and 200, such as between 25 and 100.

PCR primers as provided herein contain one or more cleavable bases. A "cleavable base" refers to any base that once incorporated into a nucleic acid can be cleaved under appropriate conditions. Exemplary cleavable bases include uracil, inosine, an oxidized pyrimidine, an oxidized purine, 5-hydroxyuracil, 5-hydroxymethyl uracil, 5-formyluracil, 7-methylguanine, 8-oxo-guanine, xanthine, hypoxanthine, 5,6-dihydrouracil, and 5-methylcytosine. A preferred cleavable base is uracil.

A cleavable base may be removed from a nucleic acid sequence (e.g., a primer sequence in an amplification product) by enzymatic, thermal, chemical, photo-oxidative, or other treatments. For example, uracil may be removed by a uracil glycosylase; methylate cytosine may be cleaved by sodium bisulfite treatment; uracil, 5-hydroxyuracil, 5-hydroxymethyluracil, and 5-formyluracil may be removed by hSMUG1; and inosine may be removed by Endo V or human alkyladenine DNA glycosylase (hAAG). The enzymes or chemicals useful in removing cleavable bases from nucleic acid sequences are referred to as "cleaving reagents."

A preferred cleaving reagent is UNG. UNG is an enzyme that catalyzes the release of free uracil from single stranded and double stranded DNA of greater than 6 base-pairs. It functions by removing uracil residues from PCR amplification products to yield apyrimidic sites. These sites are susceptible to hydrolysis by heat or alkaline treatment, resulting in degradation of the DNA at any uracil-containing sites. The elevated heat or alkali also results in inactivation of the UDG.

The cleavable bases in PCR primers of the present disclosure are preferably at a location with a minimal distance away from the 3' termini of the primers that these bases are present. The minimal distance between a cleavable base and the 3' terminus of the primer that comprises the cleavable base may be 4, 5, 6, 7, 8, or more nucleotides. Preferably, the minimal distance is at least 4 nucleotides. In other words, the cleavable base is at least 4 nucleotides away from the 3' terminus of the primer that comprises the cleavable base. In certain other embodiments, the minimal distance is at least 5 nucleotides. In certain other embodiments, the minimal distance is at least 6 nucleotides. In certain other embodiments, the minimal distance is at least 7 nucleotides. In certain other embodiments, the minimal distance is at least 8 nucleotides.

A nucleotide that is "n" nucleotides away from the 3' terminus of a primer if the nucleotide is at the "n+1" position from the 3' terminus of the primer. For example, a nucleotide that is 4 nucleotides away from the 3' terminus of a primer if the nucleotide is the $5^{th}$ nucleotide counting from the 3' terminus of the primer.

Similarly, a base that is "n" bases or nucleotides away from the 3' terminus of a primer if the base is the base of the nucleotide at the "n+1" position from the 3' terminus of the primer. For example, a base that is 4 bases or nucleotides away from the 3' terminus of a primer if the base is the base of the $5^{th}$ nucleotide from the 3' terminus of the primer.

For singleplex PCR, one or preferably both primers contain one or more cleavable bases.

For multiplex PCR, substantially all (e.g., at least 80%, at least 85%, at least 90%, or at least 95%) of the primers as provided herein contain one or more cleavable bases. Preferably, all of the primers contain one or more cleavable bases.

For singleplex PCR, in one or preferably both primers, each of the cleavable bases is at a location with a minimal distance to the 3' termini of the primers where these bases are present.

For multiplex PCR, in substantially all (i.e., at least 80%, such as at least 85%, at least 90%, or at least 95%) of the primers as provided herein, each of the cleavable bases is at a location with a minimal distance to the 3' termini of the primers where these bases are present. Preferably, in substantially all (i.e., at least 80%, such as at least 85%, at least 90%, or at least 95%) of the primers for performing multiplex PCR as provided herein, each of the cleavable bases is at least 4 nucleotides away from the 3' termini of the primer where the base is present. More preferably, in all of the primers, each of the cleavable bases is at least 4 nucleotides away from the 3' termini of the primer where the base is present.

In certain other embodiments, in substantially all (i.e., at least 80%, such as at least 85%, at least 90%, or at least 95%) of the primers for performing multiplex PCR as provided herein, each of the cleavable bases is at least 5 nucleotides away from the 3' termini of the primer where the base is present. More preferably, in all of the primers, each of the cleavable bases is at least 5 nucleotides away from the 3' termini of the primer where the base is present.

In certain other embodiments, in substantially all (i.e., at least 80%, such as at least 85%, at least 90%, or at least 95%) of the primers for performing multiplex PCR as provided herein, each of the cleavable bases is at least 6 nucleotides away from the 3' termini of the primer where the base is present. More preferably, in all of the primers, each of the cleavable bases is at least 6 nucleotides away from the 3' termini of the primer where the base is present.

In certain other embodiments, in substantially all (i.e., at least 80%, such as at least 85%, at least 90%, or at least 95%) of the primers for performing multiplex PCR as provided herein, each of the cleavable bases is at least 7 nucleotides away from the 3' termini of the primer where the base is present. More preferably, in all of the primers, each of the cleavable bases is at least 7 nucleotides away from the 3' termini of the primer where the base is present.

In certain other embodiments, in substantially all (i.e., at least 80%, such as at least 85%, at least 90%, or at least 95%) of the primers for performing multiplex PCR as provided herein, each of the cleavable bases is at least 8 nucleotides away from the 3' termini of the primer where the base is present. More preferably, in all of the primers, each of the cleavable bases is at least 8 nucleotides away from the 3' termini of the primer where the base is present.

A nucleotide at the 3' terminus of a primer refers to the first nucleotide from the 3' terminus of the primer. A cleavable base is close to the 3' terminus of a primer if the cleavable base is the base of the $2^{nd}$, $3^{rd}$, or $4^{th}$ nucleotide from the 3' terminus (i.e., 1, 2, or 3 nucleotides or bases away from the 3' terminus).

PCR, including singleplex and multiplex PCR, may be performed in the presence of the primer pairs described herein, target nucleic acids, a DNA polymerase, a PCR reaction buffer, and other optional components.

DNA polymerases useful for performing PCR are known in the art. The DNA polymerases are typically thermostable and may be high-fidelity polymerases or Hot Start polymerases. Exemplary DNA polymerases include Taq polymerase (from *Thermus aquaticus*), Tfi polymerase (from *Thermus filiformis*), Bst polymerase (from *Bacillus stearothermophilus*), Pfu polymerase (from *Pyrococcus furiosus*), Tth polymerase (from *Thermus thermophilus*), Pow polymerase (from *Pyrococcus woesei*), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*), Amplitaq Gold® DNA polymerase (Applied Biosciences), Stoffel fragment of Amplitaq® DNA Polymerase (Roche), KOD polymerase (EMD Biosciences), KOD Hot Start polymerase (EMD Biosciences), Deep Vent™ DNA polymerase (New England Biolabs), Phusion polymerase (New England Biolabs), Klentaq1 polymerase (DNA Polymerase Technology, Inc), Klentaq Long Accuracy polymerase (DNA Polymerase Technology, Inc), Omni KlenTaq™ DNA polymerase (DNA Polymerase Technology, Inc), Omni KlenTaq™ LA DNA polymerase (DNA Polymerase Technology, Inc), Platinum® Taq DNA Polymerase (Invitrogen), Hemo Klentaq™ (New England Biolabs), Platinum® Taq DNA Polymerase High Fidelity (Invitrogen), Platinum® Pfx (Invitrogen), Accuprime™ Pfx (Invitrogen), and Accuprime™ Taq DNA Polymerase High Fidelity (Invitrogen).

PCR reaction buffers are also known in the art. They typically include a monovalent cation (e.g., $K^+$), a buffering substance to maintain pH (e.g., Tris-HCl), and a divalent cation (e.g., $Mg^{2+}$ and $Mn^{2+}$).

Additional components that may be included in PCR reaction mixtures include, for example, one or more of the following components: dimethyl sulfoxide (DMSO), bovine serum albumin (BSA), glycerol, formamide, dimethysulfoxide, tetramethylammonium chloride, potassium glutamate, ammonium sulfate, nonionic detergents, and cationic detergents.

The number of cycles that a particular PCR may vary depending on the target nucleic acids and the amounts thereof in the sample. Typically, 5-35 cycles of heating, annealing and extension may be performed. Designing PCR cycles (e.g., multiplex PCR cycles), including designing temperatures and durations of heating, annealing and extension, and the number of cycles, are known in the art (see, Henegariu et al., BioTechniques 23: 504-11, 1997).

PCR amplification products using primers having one or more cleavable bases will contain one or more cleavable bases themselves. The methods for performing PCR provided herein may further comprise cleaving the one or more cleavable bases in the amplification product(s) to remove the cleavable bases. The removal of the cleavable bases from the amplification products results in abasic sites in the product(s).

For example, amplification product(s) that contain uracils may be treated by UNG to remove uracils from the amplification product(s) to yield abasic sites in the amplification product(s). These abasic sites are susceptible to hydrolysis by heat or alkali, which fragments the uracil-containing amplification products. The heat or alkali also results in inactivation of the UNG.

Other methods for removing cleavable bases from nucleic acids, such as amplification products obtained from PCR using primers containing cleavable bases, are known in the art and may also be used. Such methods include those described above with respect to cleavable bases, cleaving reagents, and other treatments of removing cleavable bases.

In addition to heat and alkali treatments, abasic sites in nucleic acid molecules are susceptible to other treatments, which also fragment the abasic sites-containing nucleic acids. Such treatments include treatments with one or more enzymes capable of fragmenting abasic site-containing nucleic acid at abasic sites, such as treatments by APE 1, Endonuclease III (Endo III), Endonuclease IV (Endo IV), Endonuclease VIII (Endo VIII), formamidopyrimidine DNA glycosylase (Fpg), hOGG1, and hNEIL1. The above exemplary enzymes are available from New England Biolabs.

In some embodiments, the reagents for removing cleavable bases and for subsequent fragmenting nucleic acids containing abasic sites resulting from the removal of the cleavable bases may be in the same reaction mixture. For example, uracils in a nucleic acid amplification product may be removed and the resulting product fragmented using a mixture of UDG and Endo VIII, such as USER™ (New England Biolabs). UDG catalyses the excision of a uracil base, forming an abasic site while leaving the phosphodiester backbone intact. The lyase activity of Endo VIII breaks the phosphodiester backbone at the 3' and 5' sides of the abasic site so that base-free deoxyribose is released. In subsequent steps, the short fragments resulting from the breakage of the phosphodiester backbone may be removed.

The removal of cleavable bases from an amplification product, the fragmentation of the products containing abasic sites, and the removal of resulting short nucleic acid fragments produce an amplification product having single stranded overhangs at each end. The methods for performing PCR provided herein may further comprise digesting the single-stranded overhangs, such as by treating an amplification product having single-stranded overhangs with an exonuclease to produce a trimmed, blunt-ended, double-stranded amplification product.

An exemplary exonuclease is *E. coli* Exonuclease I (Exo I). Exo I a 3' to 5' exonuclease that can be used specifically for single-stranded DNA degradation, releasing 5'-phosphate mononucleotides from the 3'-hydroxyl termini of single-stranded DNA. This 3' to 5' exonuclease is highly specific for single-stranded DNA and does not react with double-stranded DNA or RNA. It may be subsequently inactivated by, for example, heat treatment at 80° C. for 15 minutes. Additional exemplary exonucleases include Mung bean nuclease and Klenow.

Trimmed blunt-ended double-stranded amplification products from several singleplex or multiplex PCR reactions may be pooled together before further downstream treatments or analyses. Alternatively, they may be directly subject to such treatments or analyses without combining with amplification products from other PCR reactions.

Preferably, the trimmed blunted-ended double stranded amplification products are first purified before downstream treatments, such as ligated to adapters. Kits for purifying PCR products are commercially available, including QIAquick PCR Purification kit (Qiagen).

The methods for performing PCR provided herein may further comprise ligating adapters to trimmed amplification products. Such amplification products may be directly used to ligate to one or more adapters. Alternatively, they may first be modified, such as by adding adenines to their 3' ends to facilitate ligation to one or more adapters having a T overhang.

As used herein, the terms "adapter" and "adaptor" refer generally to any linear oligonucleotide that can be ligated to a nucleic acid molecule. Preferably, an adapter is not substantially complementary to target nucleic acids in a sample. Adapters may be about 10-100 nucleotides, such as about 12-60 nucleotides and about 15-50 nucleotides in length. Generally, the adapter can include any combination of nucleotides. In some embodiments, the adapter can include a barcode or tag (e.g., a specific oligonucleotide sequence) to assist with downstream cataloguing, identification or sequencing.

Methods for ligating adapters to blunt-ended nucleic acids are known in the art and may be used in generating sequencing libraries from amplification products of PCR as provided herein. Exemplary methods include those described in Sambrook J and Russell D W, editors. (2001) Molecular Cloning: A Laboratory Manual. 3rd ed. Cold Spring Harbor, N.Y.: Cold Spring Harbor Laboratory, Qiagen GeneRead™ Library Prep (L) Handbook and U.S. Patent Application Publication Nos. 2010/0197509, 2013/0005613.

Similarly, methods for ligating adapters having a T overhang with modified amplification products having adenines added to their 3' ends are also known in the art (see, e.g., Qiagen GeneRead™ Library Prep (I) Handbook).

The adapters ligated to the two ends of a blunt-ended nucleic acid may be the same or different. Preferably, they are different. In certain embodiments, one of the two adapters may carry a group (e.g., a biotin group) to facilitate the isolation of adapted nucleic acids having two different adapters. For example, two adapters, "A" and "B," are ligated to the ends of nucleic acids. Adapter "B" carries a biotin group, which facilitates the purification of homoadapted nucleic acids (NA or B/B). The biotin labeled sequencing library is captured on streptavidin beads. Nucleic acids containing the biotin labeled B adapter are bound to the streptavidin beads while homozygous, nonbiotinylated A/A adapters are washed away. The immobilized nucleic acids are denatured after which both strands of the B/B adapted nucleic acids remain immobilized by the streptavidin-biotin bond and single-strand template of the NB nucleic acids are freed and used in sequencing.

The DNA preparation with common or universal nucleic acid ends (i.e., adapters) is commonly referred to as "sequencing library." The addition of adapters allows anchoring the DNA fragments of the sequencing library to a solid surface for high throughput sequencing via sequences complementary to the adapter sequence immobilized to the solid surface.

Kits for sequencing library preparation are commercially available, such as Qiagen GeneRead Library Preparation System, including GeneRead DNA Library Core Kit, DNA Amp Kit, GeneRead Adapter Set 1-Plex/12-plex, GeneRead Size Selection Kit, and QIAquick PCR Purification Kit.

Sequencing libraries may be first amplified before being sequenced. The amplification may be performed in situ, in emulsion or in solution, including bridge PCR and emulsion PCR. Alternatively, the sequence library may directly be sequenced without amplification.

Emulsion PCR isolates individual DNA molecules along with primer-coated beads in aqueous droplets within an oil phase (see, Williams et al., Nature Methods 3:545-50, 2006). A polymerase chain reaction then coats each bead with clonal copies of the DNA molecule.

Bridge PCR amplifies DNA fragments flanked with adaptors (see, U.S. Pat. No. 5,641,658). A flat surface coated with two types of primers, corresponding to the adaptors. Amplification proceeds in cycles, with one end of each bridge tethered to the surface to form DNA colonies or DNA clusters.

Any high throughput sequencing platforms known in the art may be used to sequence the sequencing libraries that comprise portions of target nucleic acids prepared as described herein (see, Myllykangas et al., *Bioinformatics for High Throughput Sequencing*, Rodriguez-Ezpeleta et al. (eds.), Springer Science+Business Media, LLC, 2012, pages 11-25). Exemplary high throughput DNA sequencing systems include, but are not limited to, the GS FLX sequencing system originally developed by 454 Life Sciences and later acquired by Roche (Basel, Switzerland), Genome Analyzer developed by Solexa and later acquired by Illumina Inc. (San Diego, Calif.) (see, Bentley, Curr Opin Genet Dev 16:545-52, 2006; Bentley et al., Nature 456:53-59, 2008), the SOLiD sequence system by Life Technologies (Foster City, Calif.) (see, Smith et al., Nucleic Acid Res 38: e142, 2010; Valouev et al., Genome Res 18:1051-63, 2008), CGA developed by Complete Genomics and acquired by BGI (see, Drmanac et al., Science 327:78-81, 2010), PacBio RS sequencing technology developed by Pacific Biosciences (Menlo Park, Calif.) (see, Eid et al., Science 323: 133-8, 2009), and Ion Torrent developed by Life Technologies Corporation (see, U.S. Patent Application Publication Nos. 2009/0026082; 2010/0137143; and 2010/0282617).

The present disclosure also provides primer pair sets. A primer pair set provided herein comprises one or more different primer pairs, each primer pair is specific for one of a plurality of different target nucleic acids, wherein each primer of the different primer pairs contains one or more cleavable bases, and wherein in substantially all of the primers of the different primer pairs, each of one or more cleavable bases are at a location with a minimum distance away from the 3' terminus of the primer that comprises the one or more cleavable bases.

A primer pair set may comprise one primer pair, but preferably two or more primer pairs. For example, a primer pair set may comprise at least 10, 20, 30, 40, 50, 100, 200, 300, 400, 500, 600, 700, 800, 900, 1000, 1500, 2000, 2500, or 3000 different primer pairs. The maximum number of different primer pairs in a primer pair set may be 4000, 5000, 6000, 7000, 8000, 9000, 10000, or more. The number of primer pairs in a primer pair set may be between 50 and 500, between 500 and 1000, between 1000 and 2000, between 2000 and 3000, between 3000 and 4000, between 4000 and 5000, between 5000 and 6000, between 6000 and 7000, between 7000 and 8000, between 8000 and 9000, and between 9000 and 10000. The number of primer pairs in a primer pair set may also be between 100 and 10000, such as between 100 and 9000, between 200 and 8000, between 1000 and 7000, and between 2000 and 6000.

A primer pair set may comprise a primer pair specific for a single gene or region. Preferably, a primer pair set comprises primer pairs specific for different genes, different regions of one or more genes, or a combination of primer pairs specific for different genes and primer pairs specific for different regions of one or more other genes. The number of different genes that the primer pairs of a primer pair set may be between 5 and 1000, such as between 5 and 10, between 10 and 50, between 50 and 100, between 100 and 200, between 200 and 400, between 400 and 600, between 600 and 800, and between 800 and 1000. Preferably, the number of different genes to be amplified using a primer pair set is between 10 and 200, such as between 25 and 100.

A primer pair set useful for performing multiplex PCR may be in the form of a single solution where all the primer pairs in the set are present. Alternatively, the primer pair set may be in the form of multiple solutions, each of the solutions comprises multiple primer pairs (e.g., at least 10, 20, 30, 40, 50, 100, 200, 300, 400, or 500 primer pairs). The multiple solutions of the primer pair set may be combined in a single multiplex PCR reaction.

In a related aspect, the present disclosure also provides use of the primer pair sets provided herein for performing PCR (including both singleplex and multiplex PCR) and optional downstream sequencing analysis.

The present disclosure also provides a PCR reaction mixture that comprises the primer pair set provided herein. The reaction mixture additionally comprises one or more DNA polymerases, a PCR reaction buffer, dNTPs, and one or more other optional agents (e.g., stabilizing agents such as gelatin and bovine serum albumin). The components of the PCR reaction mixture are described above with respect to performing PCR.

In a related aspect, the present disclosure also provides use of the PCR reaction mixture provided herein for performing PCR (including both singleplex and multiplex PCR) and optional downstream sequencing analysis.

The present disclosure also provides kits for performing PCR (including both singleplex and multiplex PCR) that comprise the primer pair sets provided herein.

The kits may further comprise a mixture that comprises dNTPs and a PCR reaction buffer. The PCR reaction buffer may include a buffering substance (e.g., Tris-HCl), a monovalent cation (e.g., $K^+$), a divalent cation (e.g., $Mg^{2+}$ and $Mn^{2+}$), dNTPs, and optionally other agents (e.g., stabilizing agents such as gelatin and bovine serum albumin).

The kits may further comprise a DNA polymerase.

The kits may further comprise a cleaving reagent capable of cleaving the cleavable bases in the primer pairs of the primer pair set in the kits.

The kits may also further comprise one or more of the following additional components: an enzyme capable of fragmenting abasic site-containing nucleic acids at the abasic sites (e.g., Endo III, Endo IV, and Endo VIII), an exonuclease capable of degrading single-stranded overhangs (e.g., Exo I), and a ligase.

In a related aspect, the present disclosure also provides use of the kit provided herein for performing PCR (including both singleplex and multiplex PCR) and optional downstream sequencing analysis.

The methods, primer pair sets, PCR reaction mixtures, and kits for performing PCR provided herein are useful for single nucleotide polymorphism (SNP) analysis, genotyping, copy number variation analysis, epigenetic analysis, gene expression analysis, hybridization arrays, analysis of gene mutations (e.g., substitutions, insertions, inversions, point mutations, deletions, mismatches and translocations) for detection, prognosis, and diagnosis of diseases (e.g., cancer, neurological disease, heritable diseases, developmental disorders, and many others), nucleic acid sequencing, and the like.

The following examples are for illustration, and are not limiting.

Example 1

FIG. 4 shows an example of alignment problems near the ends of a read. The reads for this example were generated via target enrichment without primer digestion. The original reads have the complete primer sequence. The sample had a 3-nucleotide deletion that happens to be very close to one end of the insert in one of the amplicons. The bottom panel in the figure shows that the alignment of these original reads to the reference genome. It can be seen that the reads align correctly and the deletion is clearly apparent from the alignments.

To show the effect of the removing the primer bases, the inventor removed the primer bases from the reads and aligned them to a reference genome. The top panel in the figure shows the alignment of these trimmed reads. It is clear from the figure that the reads without the primer bases (i.e., trimmed reads) are misaligned to the reference. The deletion does not appear any more, and instead a single nucleotide mismatch can be seen in place of the deletion. The lack of primer bases caused misalignments towards the end of the trimmed reads, which resulted in missing the deletion altogether and incorrectly calling a SNP instead.

Example 2

Figure 6:
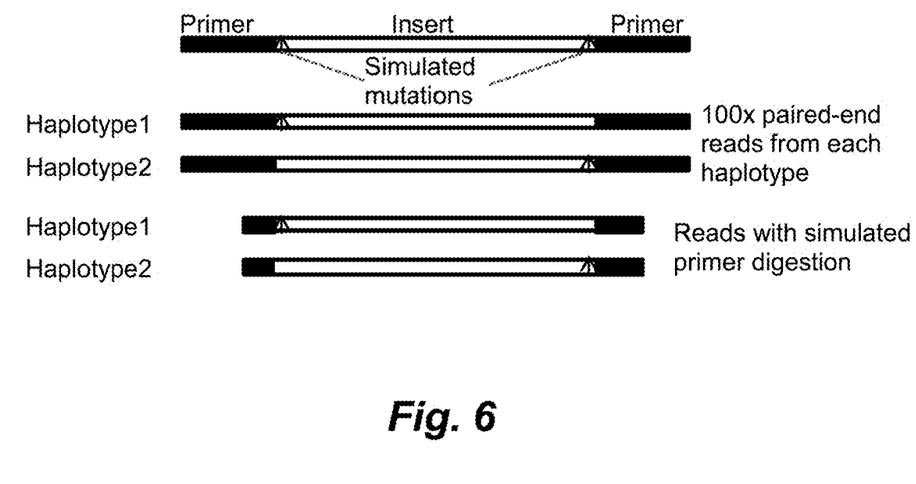
FIG. 6 is a schematic representation of generating simulating reads with mutations at each end of an amplicon insert.

A simulation study was conducted to empirically evaluate the effect of distance from the edge of read on the ability to call a variant. This simulation was to create simulated data with variants at the ends of each amplicon insert and primer digestion at varying distances from the amplicon insert, and to observe how many of these variants could be recovered through a standard analysis pipeline in each case. A panel targeting coding regions of 32 genes of high interest in studying prostate cancer was designed and consisted of 1,850 primer pairs. For each amplicon, a point mutation at each end of the amplicon insert was generated by randomly mutating the base at that position to one of the three non-reference bases at that position. Two haplotype sequences were generated from the complete sequence of each amplicon by incorporating exactly one mutation into each haplotype. Next, simulated paired-end Illumina reads at 100× read-depth from each haplotype were generated using the ART read simulator (Huang et al., Bioinformatics 28:593-4, 2012). In the primer design, one to three amplicons overlapped any base in the target region. Hence, the actual allele frequencies of the simulated variants were 50%, 25% or 16.67%, respectively, based on whether 1, 2, or 3 amplicons covered that position in the target. Primer digestion on these reads were simulated by trimming primer bases up to first Thymine base that was at least d bases away from the 3' end of the primer, for variable values of d (d={1, 2, 3, 4, 5}). This process is illustrated in FIG. 6.

A standard pipeline that involved read alignment with BWA MEM (Li and Durbin, Bioinformatics 25:1754-60, 2009), post-processing of the alignments with GATK indel realigner and GATK base quality score recalibrator, trimming of the residual primer bases using custom scripts, and variant calling with GATK Unified Genotyper (DePristo et al., Nat Genet 13:191-8, 2011) was used to analyze the data. The software used for the major steps in the pipeline and the parameters used to run these programs are listed below:

| Step | Program | Parameters |
| --- | --- | --- |
| Alignment | BWA MEM, version: 0.7.5a-r422 | bwa mem -M -L 1000, 5 -t 8 |
| Indel Realignment | GATK Lite version 2.3-9, GATK Indel realigner | T RealignerTargetCreator --baq OFF -nt 8 -o realign.intervals -L primers.bed<br>T IndelRealigner --baq OFF -targetIntervals realign.intervals -L primers.bed |
| Base Quality Recalibration | GATK Lite version 2.3-9, GATK Base Quality Recalibrator | T BaseRecalibrator --disable_indel_quals -knownSites simulated_mutations.vcf -L primers.bed -o recal.grp<br>T PrintReads -BQSR recal.grp |
| Primer trimming | Custom scripts tp trim away residual primer bases | N/A |
| Variant Calling | GATK Lite version 2.3-9, GATK Unified Genotyper | T UnifiedGenotyper -L primers.bed -dcov 2500 -glm BOTH --min_base_quality_score 17 --standard_min_confidence_threshold_for_calling 30.0 --standard_min_confidence_threshold_for_emitting |

| Step | Program | Parameters |
|---|---|---|
| | | 30.0 --baq CALCULATE_AS_NECESSARY --baqGapOpenPenalty 30.0 --defaultBaseQualities -1 -nt 8 |

The resulting variant calls were analyzed to study the effect of primer digestion on recoverability of the simulated variants. The results from this analysis (see, FIG. 7) show that only 82% of the simulated variants could be recovered (called from the simulated data) for d=1 (i.e., when the minimum distance of the simulated Uracil base from the 3' end of the primer is 1). Only 97% of the simulated variants were recoverable at d=2. In contrast, as many as 99.75% of the simulated variants were recoverable at d=5.

Figure 7:
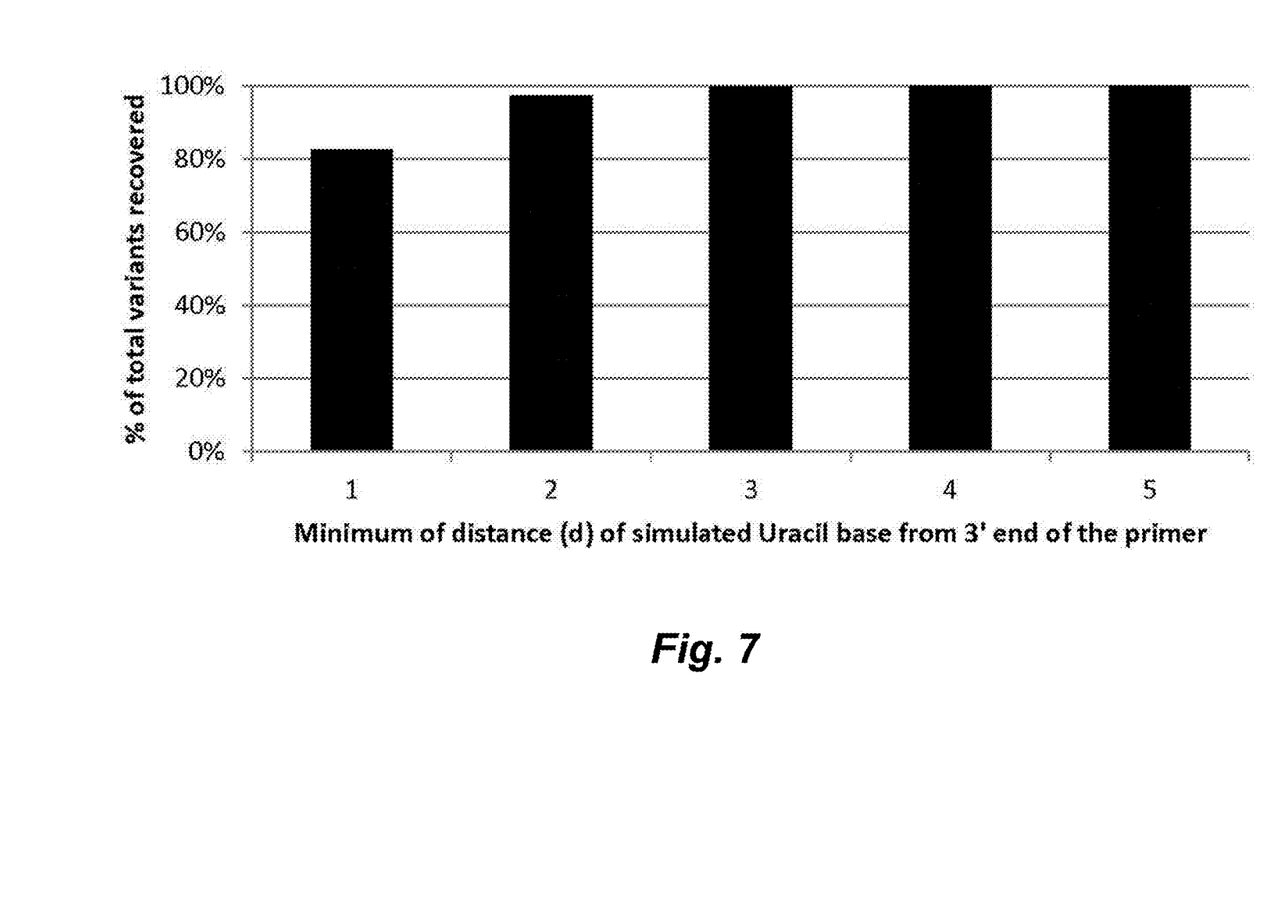
FIG. 7 is a graph showing recoverability of simulated variants for different values of minimum distance (d) of simulated uracil bases from the 3' ends of primers.
Figure 8:
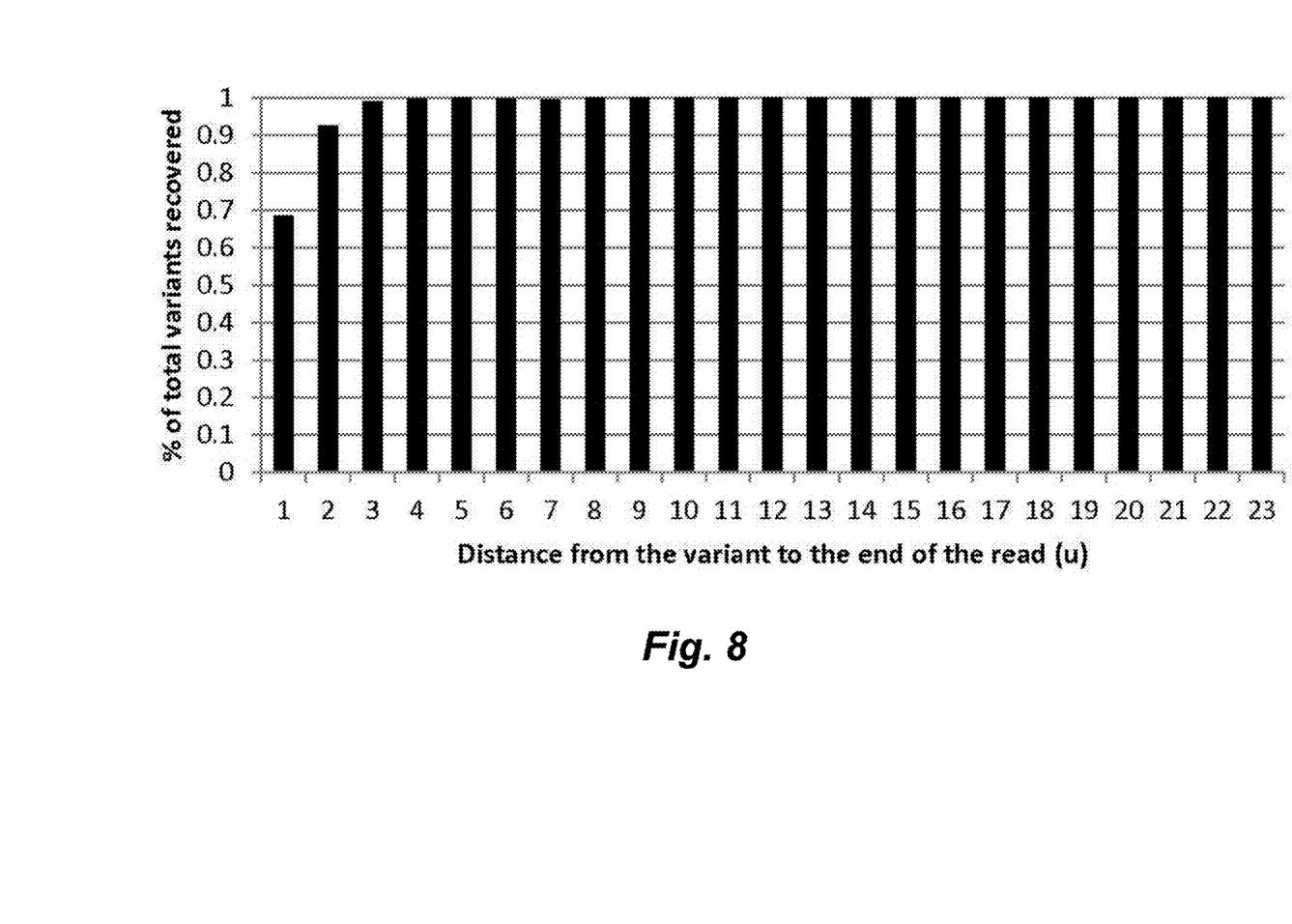
FIG. 8 is a graph showing recoverability of simulated variants for different values of distances from simulated variants to the ends of reads (u).

The results in FIG. 7 were based on minimum distance of the simulated Uracil base from the 3' end of the primer. The actual position of the simulated Uracil base depended on the primer sequence and the position of the first Thymine base beyond the minimum distance within primer sequence. Therefore, for any value of d, the actual distance between variant (which was at the end of the amplicon insert as shown in FIG. 6) and the simulated uracil base (denoted by u) could be much greater than d. Analysis of recoverability of variants with actual distance from the end of the read u would help in determining the actual minimum distance threshold d that was optimal. To this end, the simulation results from all the different values of d were combined, and the recoverability based on u irrespective of the actual value of d used for the simulated primer digestion was tabulated. These results (see, FIG. 8 and the table below) show that only 68% of the simulated variants were recoverable when the variant is only 1 bp away from the end of the read. Less than 99% of the variants were recoverable for all values of u<3. All simulated variants were recoverable for values of u>7. Small numbers of variants were non-recoverable for u between 4 and 6. Based on these results, the minimum value of d used for primer digestion should be 4 to ensure at least 99% of the possible variants are recovered. Preferably, d should be >7 to ensure that 100% of the possible variants could be recovered.

Number of simulated variants and their recoverability for different values of u

| u | No. of Simulated variants | Recovered variants | Fraction of variants recovered | Missed variants |
|---|---|---|---|---|
| 1 | 1339 | 914 | 0.682599 | 425 |
| 2 | 1113 | 1027 | 0.922731 | 86 |
| 3 | 1060 | 1048 | 0.988679 | 12 |
| 4 | 996 | 991 | 0.99498 | 5 |
| 5 | 950 | 948 | 0.997895 | 2 |
| 6 | 757 | 754 | 0.996037 | 3 |
| 7 | 545 | 541 | 0.992661 | 4 |
| 8 | 348 | 348 | 1 | 0 |
| 9 | 303 | 303 | 1 | 0 |
| 10 | 200 | 200 | 1 | 0 |
| 11 | 152 | 152 | 1 | 0 |
| 12 | 98 | 98 | 1 | 0 |
| 13 | 71 | 71 | 1 | 0 |
| 14 | 44 | 44 | 1 | 0 |
| 15 | 46 | 46 | 1 | 0 |
| 16 | 31 | 31 | 1 | 0 |
| 17 | 36 | 36 | 1 | 0 |
| 18 | 15 | 15 | 1 | 0 |
| 19 | 27 | 27 | 1 | 0 |
| 20 | 10 | 10 | 1 | 0 |
| 21 | 8 | 8 | 1 | 0 |
| 22 | 3 | 3 | 1 | 0 |
| 23 | 2 | 2 | 1 | 0 |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for performing nucleic acid sequencing, comprising:
   a) amplifying one or more different target nucleic acids in the presence of one or more different primer pairs specific to the one or more different target nucleic acids in a single reaction mixture via polymerase chain reaction (PCR),
   wherein each primer of the one or more different primer pairs contains one or more cleavable bases, and wherein in substantially all of the primers of the one or more different primer pairs, none of the one or more cleavable bases is less than 4 nucleotides away from the 3' terminus of the primer that comprises the one or more cleavable bases,
   b) cleaving the one or more cleavable bases in the amplification product(s) of step a) to produce single-stranded DNA overhangs in the amplification product(s),
   c) digesting the single stranded DNA overhangs obtained in step b) to generate trimmed amplification product(s),
   d) ligating adapters to the trimmed amplification product(s) to produce adapter-linked trimmed amplification product(s), and
   e) sequencing the adapter-linked trimmed amplification product(s) of step d).

2. The method of claim 1, wherein step a) comprises amplifying a single target nucleic acid in the presence of a primer pair specific to the single target nucleic acid in the single reaction mixture.

3. The method of claim 1, wherein step a) comprises amplifying a plurality of different primer pairs specific to the plurality of different target nucleic acids in the single reaction mixture.

4. The method of claim 1, wherein in all of the primers of the one or more different primer pairs, each of one or more cleavable bases is at least 4, 5, 6, 7, or 8 nucleotides away from the 3' terminus of the primer that comprises the one or more cleavable bases.

5. The method of claim 1, wherein the cleavable base is uracil.

6. The method of claim 1, wherein the cleavable base is inosine, an oxidized pyrimidine, an oxidized purine, 5-hydroxyuracil, 5-hydroxylmethyluracil, or 5-formyluracil.

7. The method of claim 1, wherein the one or more different primer pairs comprise at least 100 different primer pairs.

8. The method of claim 1, wherein in substantially all of the primers of the different primer pairs, none of the one or more cleavable bases is less than 5 nucleotides away from the 3' terminus of the primer that comprises the one or more cleavable bases.

9. The method of claim 1, wherein in substantially all of the primers of the different primer pairs, none of the one or more cleavable bases is less than 6 nucleotides away from the 3' terminus of the primer that comprises the one or more cleavable bases.

* * * * *